(12) United States Patent
Geiger et al.

(10) Patent No.: US 10,709,318 B2
(45) Date of Patent: Jul. 14, 2020

(54) OPERATION ASSISTANCE SYSTEM (71) Applicant: Aktormed GmbH, Barbing (DE)

(72) Inventors: Robert Geiger, Metten (DE); Peter Kraus, Neualbenreuth (DE)

(73) Assignee: Aktormed GmbH, Barbing (DE)

( * ) Notice: Subject to any disclaimer, the term of this patent is extended or adjusted under 35 U.S.C. 154(b) by 163 days.

(21) Appl. No.: 16/106,245

(22) Filed: Aug. 21, 2018

(65) Prior Publication Data

US 2018/0353055 A1 Dec. 13, 2018

Related U.S. Application Data

(63) Continuation-in-part of application No. 14/927,742, filed on Oct. 30, 2015, now abandoned.

(30) Foreign Application Priority Data

Nov. 5, 2014 (DE) .................... 10 2014 116 103

(51) Int. Cl.
*B25J 18/04* (2006.01)
*A61B 1/00* (2006.01)
(Continued)

(52) U.S. Cl.
CPC ........ *A61B 1/00149* (2013.01); *A61B 1/0016* (2013.01); *A61B 1/04* (2013.01);
(Continued)

(58) Field of Classification Search
CPC .............. A61B 34/30; A61B 2090/508; A61B 1/00149; A61B 90/50; F16H 25/20;
(Continued)

(56) References Cited

U.S. PATENT DOCUMENTS 4,250,762 A 2/1981 Weatherby
4,506,590 A * 3/1985 Miki .................... B25J 17/0241
192/30 W (Continued)

FOREIGN PATENT DOCUMENTS

CN 101598126 12/2009
DE 69912236 8/2004
(Continued)

*Primary Examiner* — Randell J Krug
(74) *Attorney, Agent, or Firm* — Welsh Flaxman & Gitler LLC (57) ABSTRACT

An operation assistance system includes a support column as well as at least a first and second robotic arm. A lower end section of the support column is pivotally mounted about a first pivotal axis (SA1) on a base unit and controlled by a first drive unit. A first end section of the first robotic arm is pivotally mounted about a second pivotal axis (SA2) on the upper end section of the support column opposite to the base unit and controlled by a second drive unit. A first end section of the second robotic arm is pivotally mounted about a third pivotal axis (SA3) on a second end section of the first robotic arm by a third drive unit. Each drive unit is associated with a controllable magnetic brake unit by which the robotic kinematics can be uncoupled from the drive units.

9 Claims, 8 Drawing Sheets

(51) Int. Cl.
*A61B 1/04* (2006.01)
*B25J 11/00* (2006.01)
*B25J 19/00* (2006.01)
*B25J 17/02* (2006.01)
*B25J 9/12* (2006.01)
*B25J 9/10* (2006.01)
*B25J 18/00* (2006.01)
*B25J 17/00* (2006.01)
*B25J 9/04* (2006.01)
*A61B 90/50* (2016.01)
*A61B 34/30* (2016.01)
*A61B 90/57* (2016.01)

(52) U.S. Cl.
CPC .............. *A61B 34/30* (2016.02); *A61B 90/50* (2016.02); *B25J 9/046* (2013.01); *B25J 9/102* (2013.01); *B25J 9/126* (2013.01); *B25J 11/00* (2013.01); *B25J 17/00* (2013.01); *B25J 17/02* (2013.01); *B25J 18/00* (2013.01); *B25J 19/0004* (2013.01); *A61B 1/00158* (2013.01); *A61B 2090/508* (2016.02); *A61B 2090/571* (2016.02)

(58) Field of Classification Search
CPC ... F16H 25/2454; B25J 18/04; B25J 17/0241; B25J 15/0019; B25J 18/25; B25J 9/126; B25J 19/0004
USPC ........... 74/89.23, 490.01, 490.03; 901/29, 30
See application file for complete search history.

(56) References Cited

U.S. PATENT DOCUMENTS

| | | |
|---|---|---|
| 5,228,190 A | 7/1993 | Sawa |
| 5,815,640 A | 9/1998 | Wang et al. |
| 6,211,591 B1 | 4/2001 | Kowalski et al. |
| 8,714,045 B2 * | 5/2014 | Kim .................. B25J 9/102 |
| | | 74/490.03 |
| 2012/0143048 A1 | 6/2012 | Finlay |
| 2014/0251043 A1 | 9/2014 | Gale et al. |
| 2015/0230870 A1 | 8/2015 | Jiang et al. |
| 2015/0256109 A1 | 9/2015 | Guo et al. |
| 2015/0310781 A1 | 10/2015 | Fisher |

FOREIGN PATENT DOCUMENTS

| | | | |
|---|---|---|---|
| DE | 69327325 | 7/2006 | |
| DE | 102007019363 | 11/2008 | |
| DE | 102009018917 | 11/2010 | |
| EP | 2246006 | 11/2010 | |
| JP | S60-167785 A | 8/1985 | |
| JP | S61-894900 U | 6/1986 | |
| JP | H10272143 | 10/1998 | |
| JP | 2005-192743 A | 7/2005 | |
| WO | 2007/034561 A1 | 3/2007 | |
| WO | WO2008128524 | 10/2008 | |
| WO | WO-2008128524 A2 * | 10/2008 | ............. A61B 34/70 |

* cited by examiner

OPERATION ASSISTANCE SYSTEM

BACKGROUND OF THE INVENTION

The invention relates to an operation assistance system for medical interventions or operations, comprising at least one base unit and robotic kinematics connected thereto. Operation assistance systems, in particular to support medical interventions or operations, are well-known. Systems of this type are used, for example, to guide auxiliary instruments such as camera systems etc.

As an example, an operation assistance system is described in German Patent No. DE 102007019363 A1. Described is a system for guiding surgical or medical tools or instruments by means of which an endoscope comprising a camera unit can be guided in a controlled manner. The operation assistance system in this regard comprises controlled robotic kinematics by which a surgical or medical tool or instrument mounted on the free end thereof can be moved in three-dimensional space in a controlled manner. As an example, the robotic kinematics comprise at least one support column, at least one first and second robotic arm and at least one instrument support receiving the instrument holder. In order to drive the robotic kinematics about a plurality of pivotal axes, a plurality of hydraulic drive units are provided which can be controlled using appropriate delivery or withdrawal of a fluid medium. The disadvantage with hydraulic drive units of this type is that they suffer from drift, where very slight pressure oscillations in the hydraulic drive units can, over time, lead to a displacement of the robotic kinematics, which in operation assistance systems is a distinct disadvantage, leading to incorrect positioning of the surgical or medical tool or instrument mounted in an instrument holder. This deviation from a given nominal operating position should be avoided. In addition, these types of known operation assistance systems suffer from the disadvantage that they can only be uncoupled from the drive units to manually guide the surgical or medical tools or instruments mounted on the instrument holder to a very limited extent.

German Patent No. DE 102011004370 A1 discloses an articulated arm for holding medical instruments in which at least one drive unit is provided which can position the articulated arm in an active state and can be manually retracted in a passive state. In that case, the drive unit can be moved using manual force on an instrument held on the articulated arm. Disadvantageously, this articulated arm does not have any robotic kinematics, meaning that a medical instrument mounted on it is only controllable in three dimensional spaces to a very limited extent. For use in minimally invasive operations, in particular for controlled guidance or tracking of a camera unit by operators, however, an articulated arm of this type is not suitable.

SUMMARY OF THE INVENTION

Thus, it is an aim of the present invention to provide an operation assistance system for medical interventions or operations. The operation assistance system of the present invention comprises improved robotic kinematics which can be precisely and fixedly positioned for long periods and which allows the operator to move it manually in a user-friendly manner.

An essential aspect of the operation assistance system in accordance with the invention is that each drive unit is associated with a controllable magnetic brake unit, by which the robotic kinematics can be uncoupled from the drive units. In accordance with the invention, the controllable magnetic brake units are the mechanism by which the arm of the robotic kinematics are stably fixed in position, i.e. an unwanted displacement of the robotic kinematics caused by the drive units away from a given nominal position is effectively prevented. A further advantage of the present design is that the robotic kinematics is unlocked from the drive units. In the unlocked state, the drive units can be manually moved by the operator, in particular quickly and in a user-friendly manner, and brought to almost any operating position.

Advantageously, all of the controllable magnetic brake units can be activated or deactivated, approximately simultaneously, by actuating a single control element. In a preferred embodiment, in the deactivated state the controllable magnetic brake units are powered off and in the activated state the controllable magnetic brake units are supplied with current, whereupon the frictional engagement or traction produced in the powered off state between the respective drive unit and the magnetic brake unit is removed, and thus the drive unit is unlocked. Thus, the entire robotic kinematics can be unlocked by the operator in a particularly user-friendly manner by actuating a control element.

Advantageously, the second and/or third drive unit is formed by a linear drive unit which is configured to produce a linear actuating motion orientated along the support column or along the first robotic arm. In this regard, in order to transform the respectively produced linear actuating motion into a rotary or pivotal movement about the second and/or third pivotal axis, a swivel joint comprising a crankshaft-like actuating element is operatively connected to the respective linear drive unit. Preferably, the linear drive unit is a spindle motor unit which, for example, comprises a motor unit, a transmission unit and a threaded spindle.

In an advantageous embodiment, a magnetic brake unit comprises at least one magnetic brake accommodated in a housing, preferably in a manner which is secure against rotation, which comprises a front frictional surface. In one alternate embodiment, the threaded nut which is operationally connected to the threaded spindle is accommodated in a nut recess which is pivotally mounted in the housing by bearing units. Preferably, the nut recess comprises a front friction lining which can be brought into frictional engagement with the front frictional surface of the magnetic brake.

In a further alternate embodiment, an instrument support is disposed on the second robotic arm by an angled articulated part, wherein the angled articulated part comprises an indexing shaft with a plurality of indexing lugs at the free end thereof which are operatively connected to an indexing nut disposed on the second robotic arm. The angled articulated part is preferably fixed in a manner so as to be manually pivotable about a fourth pivotal axis in a sleeve-like indexing shaft guide unit disposed on the second robotic arm.

In a preferred embodiment, the sleeve-like indexing shaft guide unit comprises a first guide or receiving channel section to receive the indexing shaft and a second guide or receiving channel section adjacent thereto to receive the indexing nut in a manner which is secure against rotation. Preferably, the indexing shaft is spring-loaded in the direction of the indexing nut by at least one spring element. In this manner, the operator has much improved access to the operation area, i.e. collisions between manually actuated operation instruments and the instrument support disposed on the robotic kinematics can thus be avoided in a non-problematic manner.

In an advantageous embodiment, the sleeve-like indexing shaft guide unit comprises a control panel with a plurality of switch or control elements. The control element contains, inter alia, the control element for approximately simultaneous actuation of the controllable magnetic brake units.

The expressions "approximately", "essentially" or "about" as used in the context of the invention mean discrepancies from the respective exact value of ±10%, preferably ±5% and/or discrepancies in the form of changes which are irrelevant to the function.

Further embodiments, advantages and application possibilities of the invention will become apparent from the following description of embodiments and from the figures. In this regard, all of the features described and/or illustrated, by themselves or in any combination, principally constitute the subject matter of the invention, independently of their recapitulation in the claims or their dependencies.

BRIEF DESCRIPTION OF THE DRAWINGS

The invention will now be described in more detail with reference to embodiments and to the drawings, in which.

DETAILED DESCRIPTION OF THE INVENTION

Figure 1:
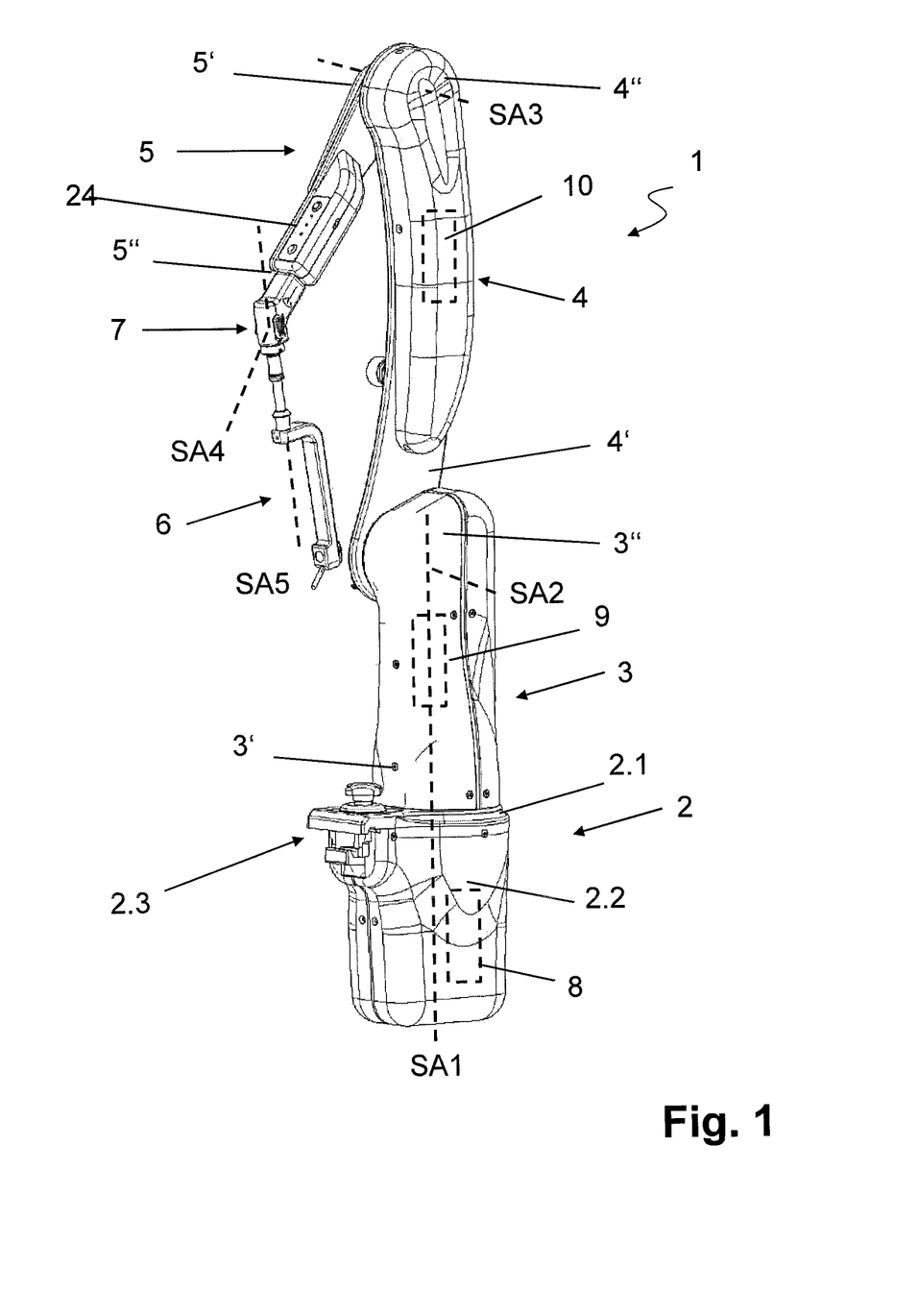
FIG. 1 shows a perspective view of an operation assistance system in accordance with the invention.

FIG. 1 shows an operation assistance system 1 configured in accordance with the invention for medical interventions or operations for guiding medical, in particular surgical tools and instruments. The term "medical tool or instrument" as used in the context of the invention should in particular be understood to include a camera unit which is mounted on an endoscope and is introduced during a minimally invasive operation via a small format operation opening ("trocar") into an operating region inside a patient's body.

Other comparable medical application possibilities wherein highly accurate guidance and/or stable fixation of a medical tool or instrument along a given guide path and/or to a given operation position are required may be envisaged without departing from the inventive concept of the invention.

The operation assistance system 1 includes a base unit 2 and robotic kinematics comprising a support column 3, first and second robotic arms 4, 5 and possibly an instrument support 6, wherein the instrument support 6 is, for example, articulated upon the second robotic arm 5, and preferably by means of an angled articulated part 7. The instrument support 6 is, for example, configured to directly receive the medical tool or instrument or to indirectly receive it by an instrument holder. A preferred construction of the robotic kinematics can be seen in the perspective representation of the operation assistance system 1 in FIG. 1.

The base unit 2 comprises a carrier plate 2.1, a base housing 2.2 which is preferably in several parts and at least one fixing element 2.3, by which the operation assistance system 1 or the base unit 2 can be fixed to the side of an operating table, for example (not shown). At least one control unit and possibly other functional units (not shown in the figures) are disposed in the base housing 2.2.

The support column 3 has lower and an upper end sections 3', 3". The base unit 2 of the operation assistance system 1 is pivotally connected about a first pivotal axis SA1 to the lower end section 3' of the support column 3 of the robotic kinematics and is controlled by a first drive unit 8. The first pivotal axis SA1 is thus vertical to the plane of the operation assistance system 1 table or the operating plane or plane of the operating table.

Furthermore, the first robotic arm 4 comprises first and second end sections 4', 4". The first end section 4' of the first robotic arm 4 is pivotally connected about a second pivotal axis SA2 to the end section 3" of the support column 3 which is opposite to the base unit 2 and controlled by a second drive unit 9. The second end section 4" of the first robotic arm 4 is pivotally connected about a third pivotal axis SA3 to a first end section 5' of the second robotic arm 5 and controlled by a third drive unit 10. The second robotic arm 5 comprises a second end section 5" opposite to the first end section 5' on which, in the present embodiment, the angled articulated part 7 is pivotable about a fourth pivotal axis SA4. The angled articulated part 7 is configured for pivotable and releasable receipt of a connecting section 6' of the instrument support 6, in fact about a fifth pivotal axis SA5. The opposing free end 6" of the instrument support 6 forms an instrument recess.

In the present embodiment, the first to third drive units 8-10 are preferably independently controllable via at least one control unit in order to effect a rotary or pivoting movement of the robotic kinematics about at least the first to third pivotal axes SA1 to SA3. Preferably, the second and third pivotal axes SA2, SA3 are parallel to each other, whereas the orientation of the first pivotal axis SA1 is perpendicular to the second or third pivotal axis SA2, SA3. The first drive unit 8 is preferably accommodated in the base housing 2.2 and the second drive unit 9 is either disposed laterally on the support column 3 or integrated into or accommodated in the support column 3. In similar manner, the third drive unit 10 is either disposed laterally on the first robotic arm 4 or integrated into it or accommodated in it.

The support column 3 extends vertically, in fact essentially along the first pivotal axis SA1, i.e. it is approximately pivotable about its own longitudinal axis. The first and second robotic arms 4, 5 extend essentially in a straight line which preferably runs perpendicular to the second or third pivotal axis SA2, SA3. In the present embodiment, at least the first robotic arm 4 is slightly curved.

In accordance with the invention, the second and/or third drive units 9, 10 are formed by a linear drive unit which is configured to produce a linear actuating motion AB orientated along the longitudinal axis of the support column 3 or the first pivotal axis SA1 and/or the first robotic arm 4. In order to transform the linear actuating motion AB produced thereby into a pivotal or rotary movement about the second and/or third pivotal axis SA2, SA3, a swivel joint 11 is provided which is in operative engagement with the respective linear drive units 9, 10 and comprises a crankshaft-like drive element 12. In a preferred variational embodiment, the linear drive unit is formed as a spindle motor unit.

In the present embodiment, the respective second and/or third drive units 9, 10, each formed as a linear drive unit, comprise a motor unit, preferably an electric motor unit 13 which is in operative engagement with a motor brake unit 14. A transmission unit 15 is connected to the motor unit 13 via which a threaded spindle 16 is set in rotation.

Figure 2:
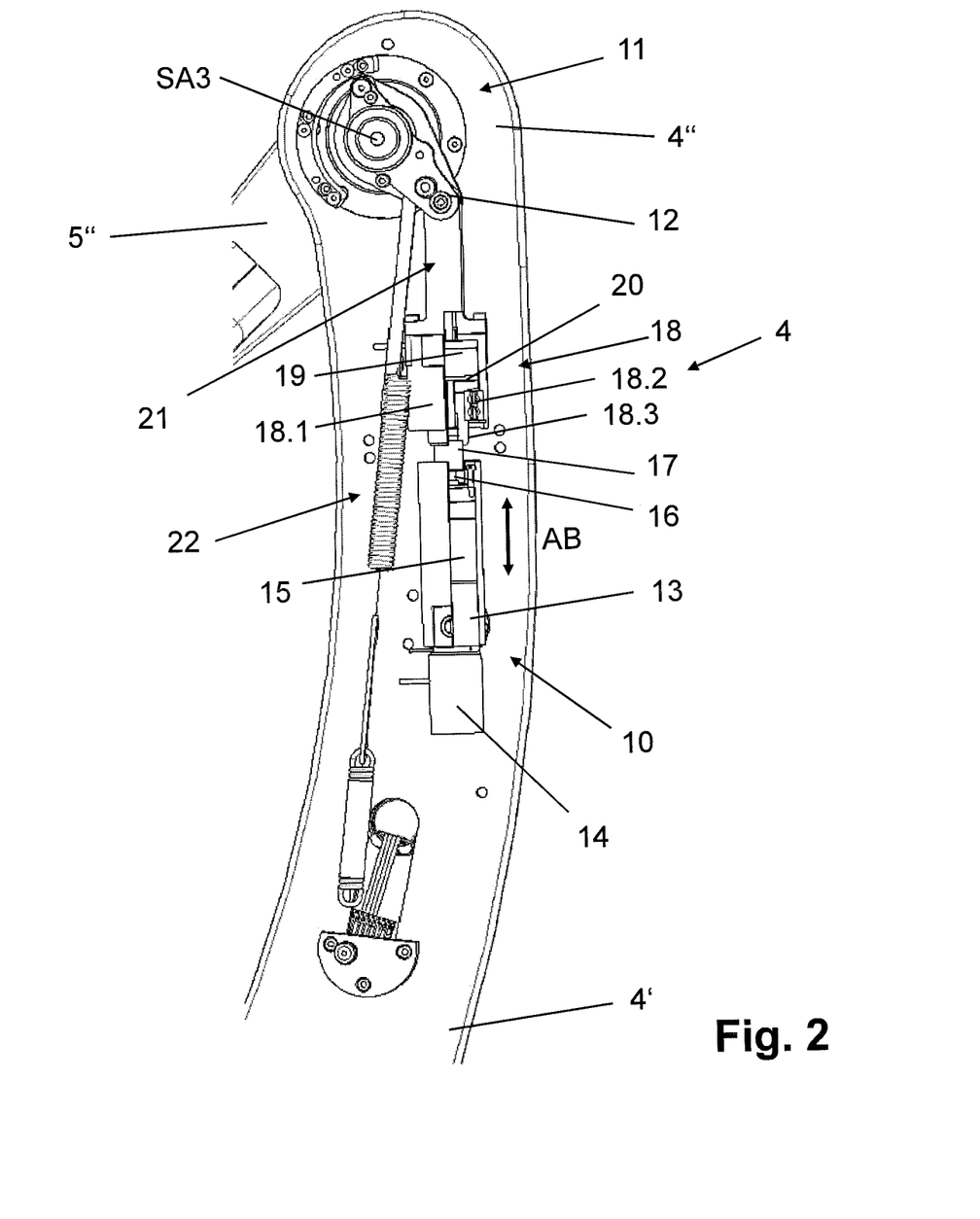
FIG. 2 shows a diagrammatic longitudinal section through the first robotic arm of the robotic kinematics.
Figure 3:
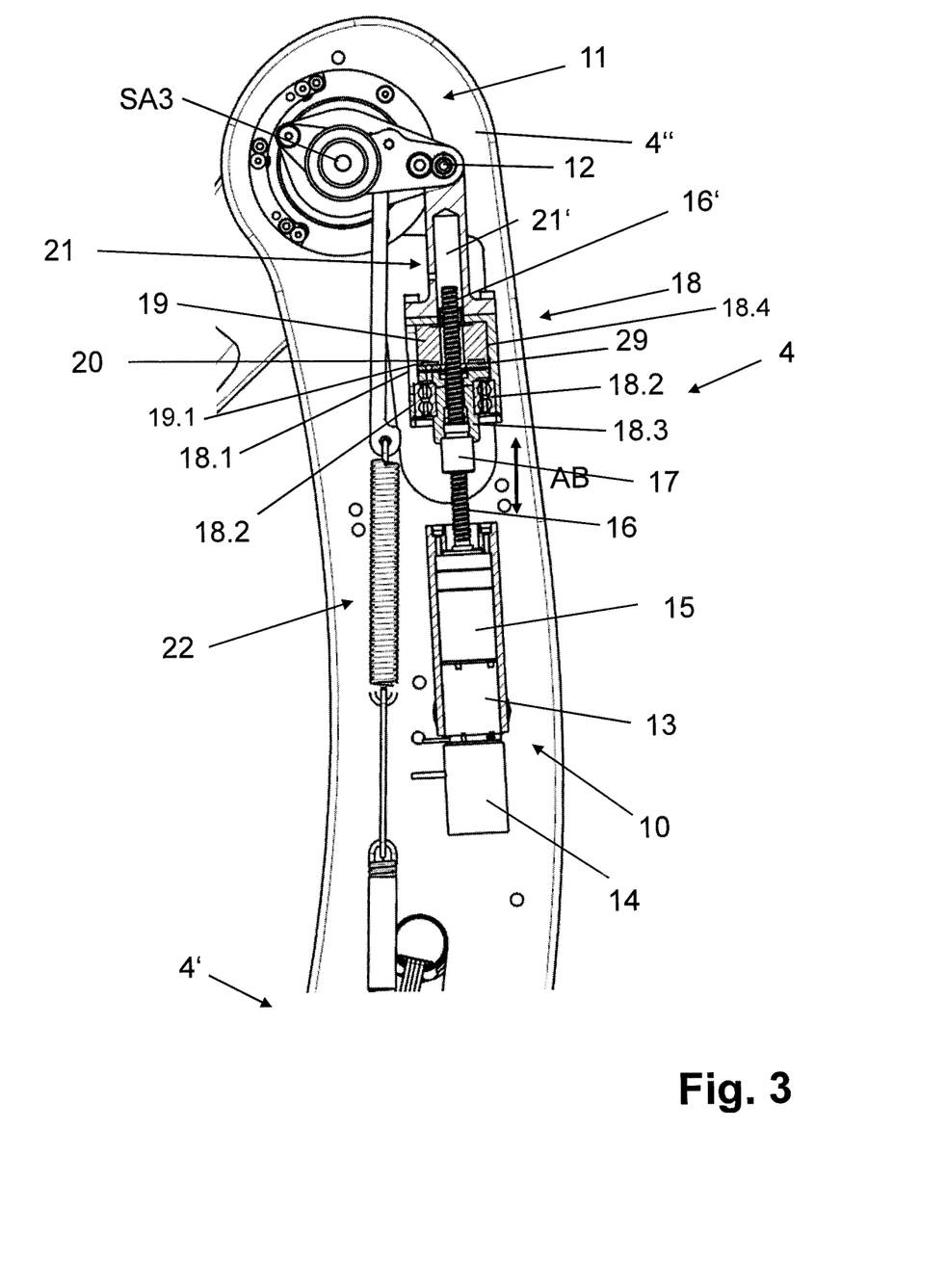
FIG. 3 shows a more detailed view of the diagrammatic longitudinal section through the first robotic arm of the robotic kinematics of FIG. 2.

As exemplary shown in FIGS. 2 and 3 the threaded spindle 16 is connected to a controllable magnetic brake unit 18 via a spindle nut 17. The magnetic brake unit 18 comprises a housing 18.1 which preferably extends concentrically about the threaded spindle 16 and in which the threaded spindle 16 with its free end 16' opposite the linear motor unit 9, 10 is at least partially accommodated. The spindle nut 17 is pivotally mounted in the housing 18.1 via bearing units 18.2, in fact by a nut pickup 18.3. The housing 18.1 is connected via connecting rod 21 with the crankshaft-like drive element 12, wherein the connecting rod 21 preferably comprises a blind hole 21'. The free end 16' of the threaded spindle 16 is at least partly accommodated in the blind hole 21' of the connecting rod 21.

Preferably, the nut pickup 18.3 is formed as a sleeve and is at least partially accommodated in the housing 18.1 and pivotally mounted therein by means of the bearing units 18.2. The threaded spindle 16 extends through the sleeve-like nut pickup 18.3 along the longitudinal axis of the housing 18.1 and via a through hole 18.4 of the housing 18.1 into the blind hole 21' of the connecting rod 21. At the free front end of the nut pickup 18.3 opposite to the spindle nut 17 there is a friction lining 29 forming a frictional surface 20. Connected to the nut pickup 18.3 along the threaded spindle 16 there is a magnetic brake 19 which is also accommodated in the housing 18.1 and is connected thereto in a non-rotatable manner, which can be brought into frictional engagement with the friction lining 29 of the nut pickup 18.3 with the magnetic brake 19 via the front frictional surface 20. When there is frictional engagement between the nut pickup 18.3 and the magnetic brake 19, the rotational movement of the threaded spindle 16 produced by the motor unit 13 is transformed into a linear movement of the magnetic brake unit 18 which in turn is connected via the connecting rod 21 with the free shaft end of the crankshaft drive element 12. The linear actuating motion AR is transformed via the crankshaft drive element 12 into a pivotal or rotational movement about the second or third pivotal axes SA2, SA3. To compensate for the dead weight of the second robotic arm 4 shown in an exemplary manner in FIG. 2, a spring arrangement 22 may be provided, for example. The spring arrangement 22 constitutes an elastic connection between the crankshaft-like drive element 12 and the opposing first end section 4' of the second robotic arm 4. The dimensions of the spring arrangement 22 are preferably such that in the unlocked state of the robotic kinematics, the operator can move it since its weight is balanced, or the robotic arms 4, 5 can be moved in space and in fact independently of the actual angular position of the swivel joint 11.

Figure 4:
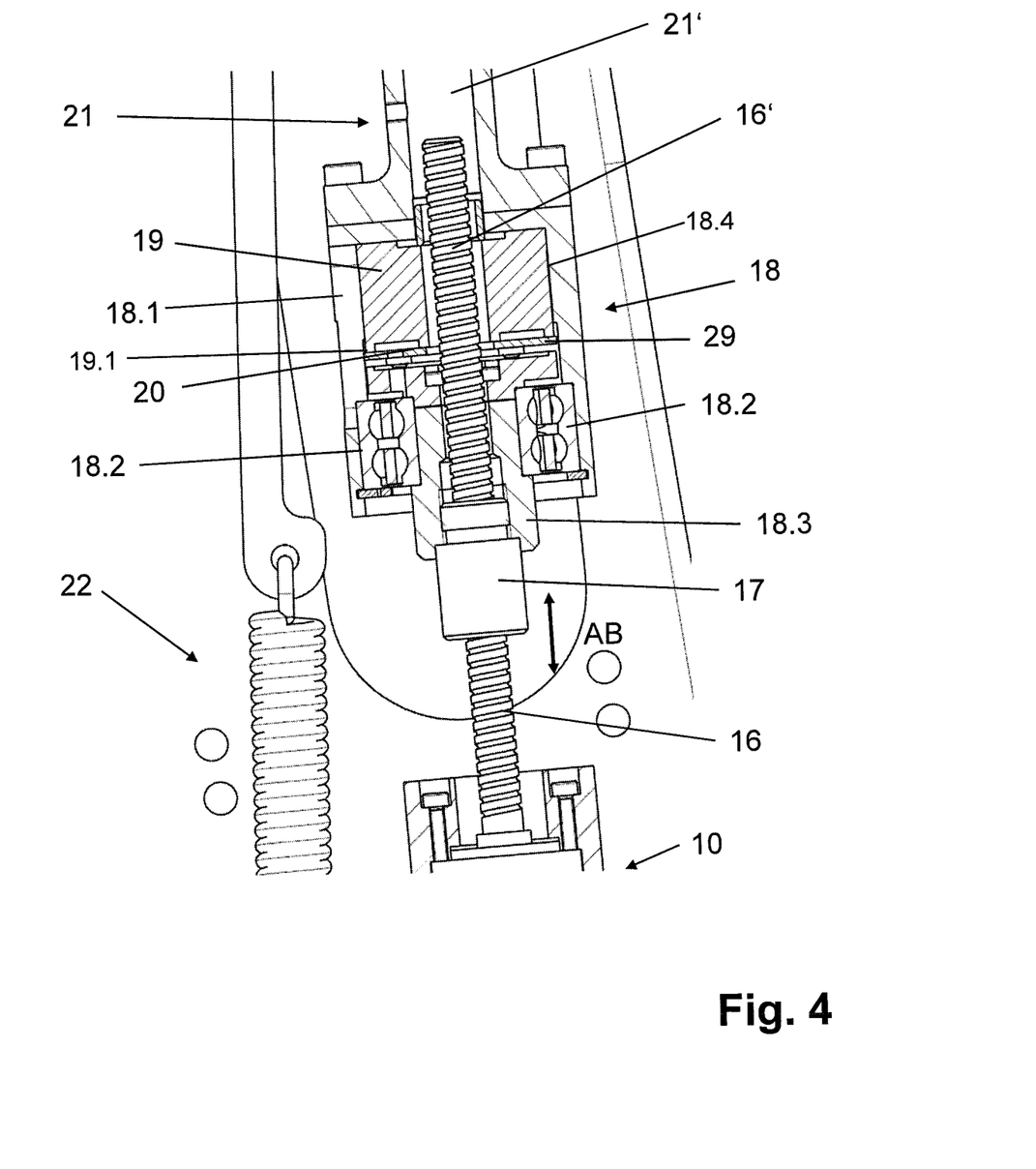
FIG. 4 shows a more detailed diagrammatic longitudinal section through the magnetic brake unit and the drive unit of the first robotic arm of FIG. 3 being mechanically coupled.
Figure 5:
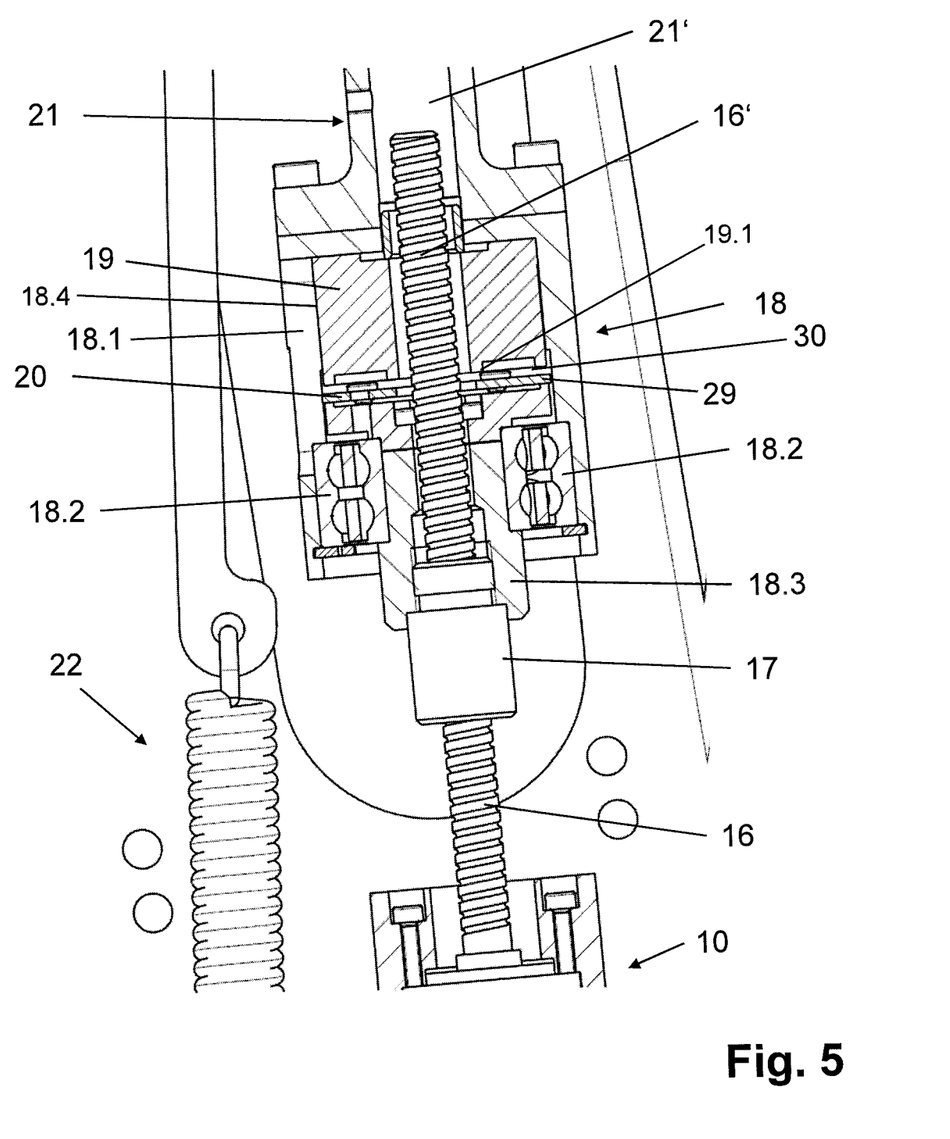
FIG. 5 shows a more detailed diagrammatic longitudinal section through the magnetic brake unit and the drive unit of the first robotic arm of FIG. 3 in the mechanically uncoupled or decoupled stage.

FIGS. 4 and 5 show a more detailed diagrammatic longitudinal section through the mechanical coupling mechanism between the magnetic brake unit and the drive unit of the first robotic arm according to FIG. 3. In FIG. 4 the magnetic brake 19 is mechanically coupled to the third drive unit 10. Thereto the friction lining 29 of the nut pickup 18.3 is in a fritional engangement with the front surface 19.1 of the magnetic brake 19. Preferably the frictional engangement exists in the deactivated stage of the magnetic brake 19. In the deactivated stage the magnetic brake 19 is powered off, for example in terms of an electrical magnetic brake 19 no current is supplied.

Therefore, the friction lining 29 mounted to the nut pickup 18.3 is pressed onto the front surface 19.1 of the magnetic brake 19. As the magnetic brake 19 is connected to the housing 18.1 in a non-rotatable manner the spindle nut 17 is also connected via the nut recess 18.3 and the frictional engagement between the nut recess 18.3 and the magnetic brake 19 in a non-rotatable manner. In this mechanical coupled stage the rotational movement of the threaded spindle 16 is transformed into the actuating motion AR of the magnetic brake unit 18 inside the first robotic arm 4. In that stage the longitudinal distance between the magnetic brake unit 18 and the third drive unit 10 within the first robotic arm 4 varies, namely decreases or increases.

In the mechanically uncoupled or decoupled stage of the magnetic brake unit 18 according to FIG. 5 the frictional engangement between the front surface 19.1 of the magnetic brake 19 and the friction lining 29 of the nut pickup 18.3 is released resulting in the existence of a small air gap 30 between the front surface 19.1 of the magnetic brake 19 and the friction lining 29. Therefore the magnetic brake 19 is pereferably activated and a magnetic force is applied to disconnect the front surface 19.1 of the magnetic brake 19 and the friction lining 29. In the mechanically uncoupled or decoupled stage of the magnetic brake unit 18 the nut pickup 18.3 with the spindle nut 17 is pivotably mounted in the housing 18.1 via the bearing units 18.2. Therefore rotational movement of the threaded spindle 16 is transformed into a rotation of the spindle nut 17 in the housing 18.1. In that mechanically uncoupled or decoupled stage the longitudinal distance between the magnetic brake unit 18 and the third drive unit 10 within the first robotic arm 4 is unchanged.

Figure 6:
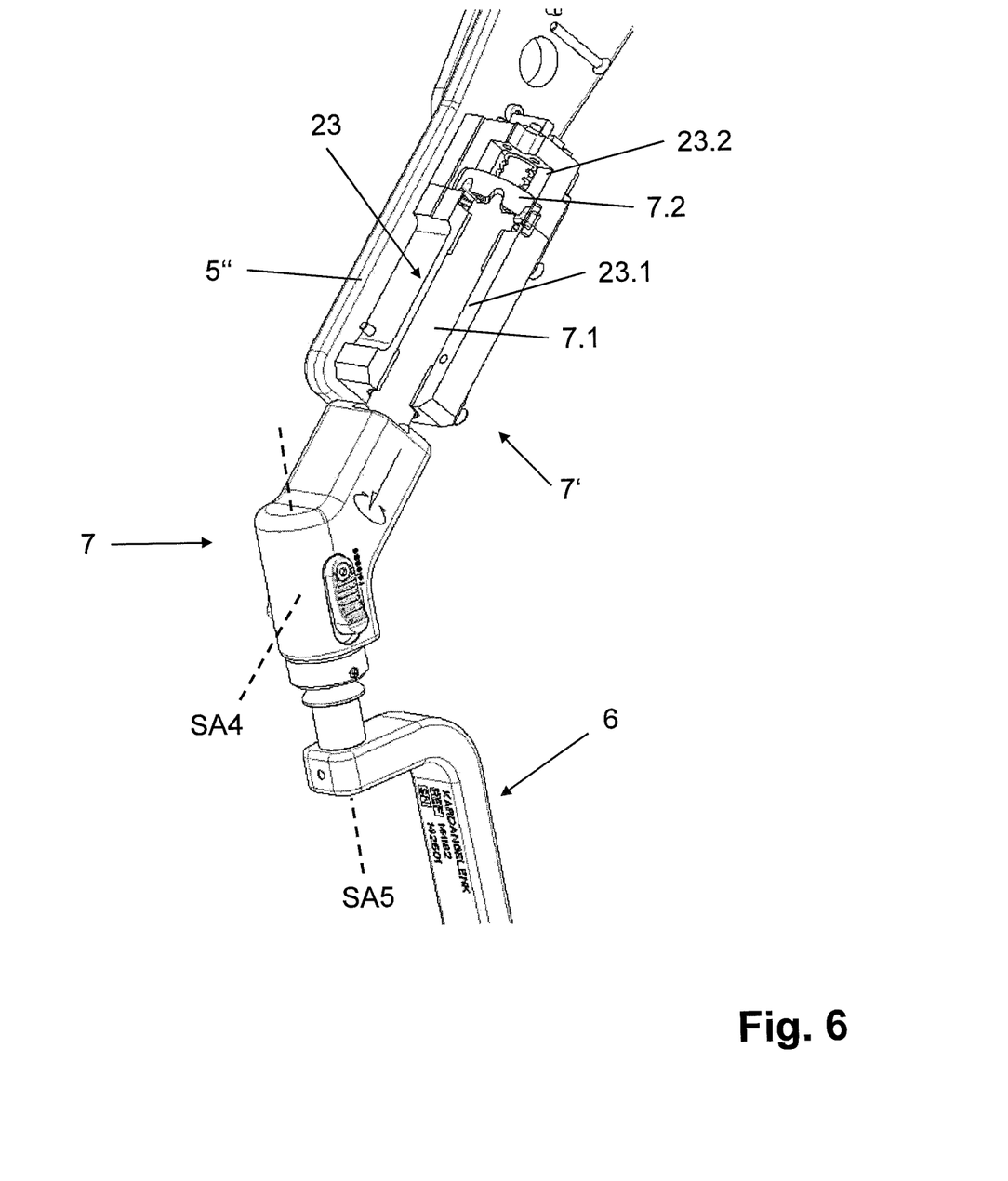
FIG. 6 shows a perspective sectional view through the indexing shaft guide unit disposed on the second robotic arm and the angled articulated part connected therewith.

FIG. 6 shows an exemplary perspective representation through the second end section 5" of the second robotic arm 5 and thus the connecting region of the angled articulated element 7. The angled articulated element 7 comprises an indexing shaft 7.1 at its upper free end 7' and an indexing nut 7.2 connected thereto. The indexing shaft 7.1 is pivotable about the fourth pivotal axis SA4 and accommodated in the second end section 5" of the second robotic arm 5, whereupon the indexing nut 7.2 is fixed against rotation in the second end section 5" of the second robotic arm 5. In order to accommodate the indexing shaft 7.1 and the indexing nut 7.2, a sleeve-like indexing shaft guide unit 23 may, for example, be disposed laterally on the second end section 5" of the second robotic arm 5, which guide comprises a first guide or receiving channel section 23.1 to receive the indexing shaft 7.1 and an adjoining second guide or receiving channel section 23.2 to receive the indexing nut 7.2. The diameter of the first guide or receiving channel section 23.1 is smaller than the diameter of the second guide or receiving channel section 23.2, so that a seat for the indexing nut element 7.2 is formed in the transitional region between the first and second guide or receiving channel sections 23.1, 23.2. The indexing nut 7.2, which is accommodated in the second guide or receiving channel section 23.2 without being able to rotate, comprises a plurality of indexing openings distributed almost uniformly about the fourth pivotal axis SA4 into which the indexing lugs at the free end of the indexing shaft 7.1 engage, thus forming a connection between the angled articulated element 7 and the indexing shaft guide unit 23 on the second robotic arm 5 which cannot pivot. Preferably, the indexing shaft 7.1 is spring-loaded by a spring element which acts in the direction of the indexing nut 7.2 and thus urges the indexing lugs at the free end into the indexing openings of the indexing nut 7.2. By appropriate manual extraction of the indexing shaft 7.1 against the resilience out of the sleeve-like indexing shaft guide unit 23, the indexing connection is released and the rotational angle about the fourth pivotal axis SA4 between the second robotic arm 5 and the angled articulated element 7 can be adjusted to the predetermined indexing positions.

In accordance with an alternate embodiment of the invention, a control panel 24 with a plurality of switch or operating elements may be disposed on the upper side of the sleeve-like indexing shaft guide unit 23 via which the operator can switch the magnetic brake unit 18 of the linear motor units 9, 10 individually or together in a manner such that this uncouples the robotic kinematics from the drive units 9, 10 and the robotic kinematics are "unlocked" from the drive units 9, 10. In the "unlocked" state, the robotic kinematics can be freely moved manually by the operator and thus can simply and easily be moved to a desired new operating position without necessitating controlling the robotic kinematics by means of the drive units 8 to 10. In the "locked" state, the robotic kinematics are locked by the magnetic brake units 18 and thus is held permanently and reliably in the given position. In this manner, operation of the operation assistance system 1 by an operator is substantially facilitated.

Preferably, in the "locked" state, the magnetic brake units 18 are powered off, so that frictional engagement between the linear motor units 9, 10 and the respective associated magnetic brake unit 18, 18* occurs. When the magnetic brake units 18, 18* are powered up, i.e. the magnetic brake units 18, 18* are activated by supplying electrical energy, the frictional engagement or the friction lock is released and the drive connection is separated. In this manner, the drive units 8 to 10 are unlocked and the robotic kinematics can be freely moved in space by the operator.

Figure 7:
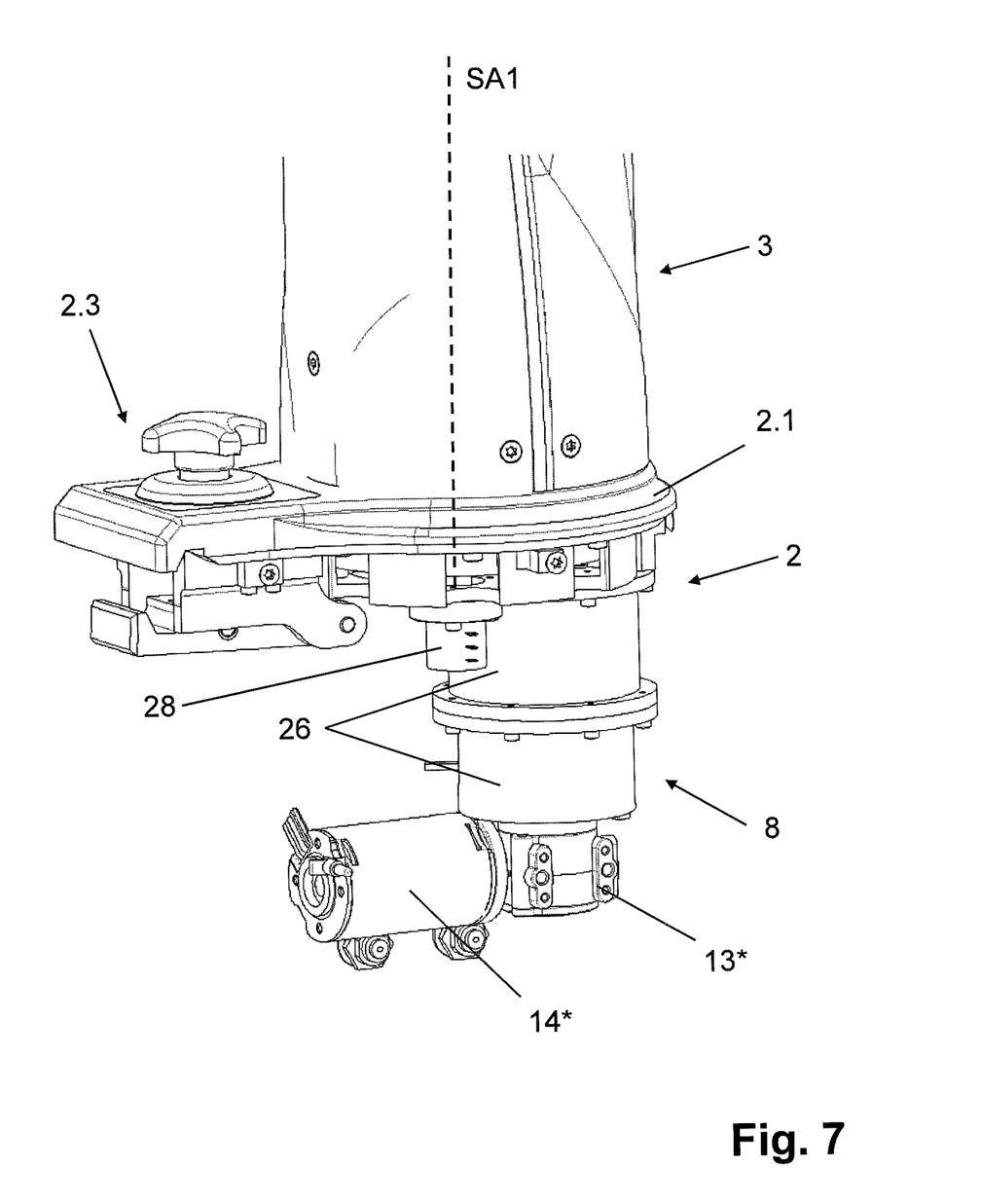
FIG. 7 shows a perspective view of the base station without the base housing.
Figure 8:
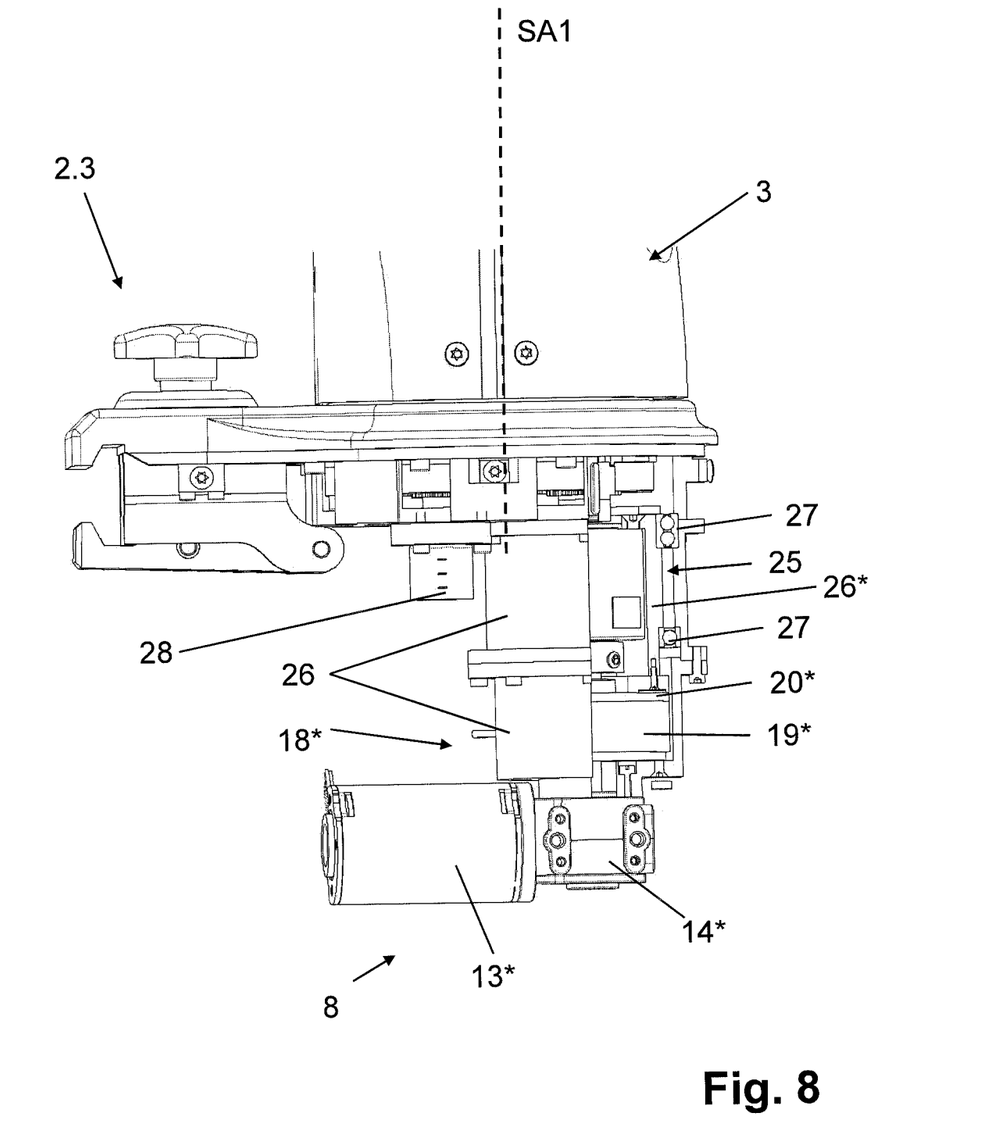
FIG. 8 shows a diagrammatic side view of the base station without the base housing with a partial sectional view through the first drive unit.

FIG. 7 shows a perspective view of the base unit 2 of the operation assistance system 1 without the base housing 2.1 in an enlarged sectional view. FIG. 8 shows a partial section along the first pivotal axis SA1 through the first drive unit 8 for actuating the support column 3 about the first, vertical pivotal axis SA1. The first drive unit 8 comprises a motor unit, preferably an electric motor unit 13*, which is connected to a transmission unit 14*.

The motor unit 13* is connected with a planetary gear unit 25 via the transmission unit 14* and a magnetic brake unit 18*, wherein the magnetic brake unit 18* and the planetary gear unit 25 are accommodated in a common outer housing 26. The planetary gear unit 25 is in turn accommodated in an inner housing 26* which is pivotally mounted in the outer housing 26 by means of bearing units 27 about a rotational axis orientated parallel to the first pivotal axis SA1. The magnetic brake unit 18* in turn comprises a magnetic brake 19* which is connected with the outer housing 26 in a non-rotational manner. In turn, the front end of the inner housing 26* has a friction lining which comprises a front frictional surface 20* to produce frictional engagement or a friction lock between the magnetic brake unit 18* and the planetary gear unit 25. Thus, the motor unit 13* can be driveably connected with the planetary gear unit 25 or uncoupled from it by powerless switching or powering off the magnetic brake unit 18*. By means of the magnetic brake unit 18*, the first drive unit 8 is also configured so as to be "unlockable".

In addition, an angle sensor unit 28 may be provided to capture the actual angular position of the support column 3 with respect to the first pivotal axis SA1.

At least the robotic arms 4, 5 of the robotic kinematics are preferably formed as hollow bodies or as plate-shaped arm elements and, for example, produced from a material which guarantees high stability and strength in order to obtain as small a mass as possible, as low a specific weight as possible and also provides a neutral material suitable for imaging or image-generating media, for example for X-rays, magnetic fields or electromagnetic waves. Preferably, a fibre-reinforced material, for example a carbon fibre-reinforced plastic, is used for robotic arms 4, 5 which are formed as hollow bodies.

The invention has been described above with reference to exemplary embodiments. Clearly, any number of modifications and changes are possible without departing from the inventive concept underlying the invention.

LIST OF REFERENCE NUMERALS 1 operation assistance system
2 base unit
2.1 base housing
2.2 fixing element
3 support column
3' lower end section
3" upper end section
4 first robotic arm
4' first end section
4" second end section
5 second robotic arm
5' first end section
5" second end section
6 instrument support
6' connection section
6" free end
7 angled articulated part
7' upper end section
7.1 indexing shaft
7.2 indexing nut
8 first drive unit
9 second drive unit
10 third drive unit
11 swivel joint
12 crankshaft-like actuating element
13, 13* motor unit
14 magnetic brake unit
14* transmission unit
15 transmission unit
16 threaded spindle
16' free end of the threaded spindle
17 spindle nut
18, 18* magnetic brake unit
18.1 Housing
18.2 bearing units
18.3 nut recess
18.4 through hole
19, 19* magnetic brake
19.1 front end
20, 20* front frictional surface
21 connecting rod
21' blind hole
22 spring arrangement
23 indexing shaft guide unit
24 control panel
25 planetary gear unit 26 outer housing
26 inner housing
27 bearing units
28 angle sensor
29 friction lining
30 air gap
AB linear actuating motion
SA1 first pivotal axis
SA2 second pivotal axis
SA3 third pivotal axis
SA4 fourth pivotal axis
SA5 fifth pivotal axis

The invention claimed is:

1. An operation assistance system for medical interventions or operations, composed of a base unit and robotic kinematics connected thereto, the robotic kinematics comprising:
    a support column having a lower end section that is pivotally mounted about a first pivotal axis on the base unit and controlled by a first drive unit;
    at least a first robotic arm; and
    a second robotic arm;
    wherein;
    a first end section of the first robotic arm is pivotally mounted about a second pivotal axis on an upper end section of the support column opposite to the base unit and controlled by a second drive unit;
    a first end section of the second robotic arm is pivotally mounted about a third pivotal axis on a second end section of the first robotic arm by a third drive unit;
    the first pivotal axis is perpendicular to the second and third pivotal axes
    each of the first drive unit, the second drive unit and the third drive unit are respectively associated with a controllable magnetic brake unit by which the robotic kinematics is selectively uncoupled from the first drive unit, the second drive unit and the third drive unit, respectively, in an uncoupled state;
    each controllable magnetic brake unit comprises at least one magnetic brake with a front frictional surface accommodated in a housing in a manner which is secure against rotation;
    the second drive unit and the third drive unit are linear drive spindle motor units;
    each of the linear drive spindle motor units comprises: a motor unit, a transmission unit, a threaded spindle, and a threaded nut operationally connected to the threaded spindle of each linear drive spindle motor unit;
    each threaded nut is accommodated in a sleeve nut pickup which is pivotally mounted by bearing units; and
    each sleeve nut pickup comprises a front friction lining brought into frictional engagement with the front frictional surface of the at least one magnetic brake of each respective controllable magnetic brake unit.

2. The operation assistance system as claimed in claim 1, wherein when the robotic kinematics are uncoupled from the first drive unit, the second drive unit and the third drive unit, the robotic kinematics are unlocked from the first drive unit, the second drive unit, and the third drive unit.

3. The operation assistance system as claimed in claim 1, wherein the controllable magnetic brake units are activated or deactivated simultaneously by actuating a single control element.

4. The operation assistance system as claimed in claim 1, wherein in order to transform produced linear actuating motion into a rotary or pivotal movement about the second and/or third pivotal axis, a swivel joint comprising a crankshaft actuating element is operatively connected to the linear drive spindle motor units.

5. The operation assistance system as claimed claim 1, wherein an instrument support is disposed on the second robotic arm by an angled articulated part.

6. The operation assistance system as claimed in claim 5, wherein the angled articulated part comprises an indexing shaft at a free end thereof which is operatively connected to an indexing nut disposed on the second robotic arm.

7. The operation assistance system as claimed in claim 5, wherein the angled articulated part is fixed to be manually pivotable about a fourth pivotal axis in a sleeve indexing shaft guide unit disposed on the second robotic arm.

8. The operation assistance system as claimed in claim 7, wherein the sleeve indexing shaft guide unit comprises a first guide or receiving channel section to receive a indexing shaft and a second guide or receiving channel section adjacent thereto to receive an indexing nut in a manner which is secure against rotation.

9. The operation assistance system as claimed in claim 7, wherein the sleeve indexing shaft guide unit comprises a control panel with a plurality of switch or control elements.

* * * * *